United States Patent
Palmas et al.

(10) Patent No.: US 7,208,649 B2
(45) Date of Patent: Apr. 24, 2007

(54) EXTERNAL SECOND STAGE CYCLONES IN OLEFIN PRODUCTION PROCESS

(75) Inventors: Paolo Palmas, Des Plaines, IL (US); Daniel N. Myers, Arlington Heights, IL (US); Richard A. Johnson, II, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 11/236,477

(22) Filed: Sep. 27, 2005

(65) Prior Publication Data
US 2006/0094917 A1    May 4, 2006

Related U.S. Application Data

(60) Provisional application No. 60/624,032, filed on Nov. 1, 2004.

(51) Int. Cl.
    *C07C 1/00*    (2006.01)
(52) U.S. Cl. .................................. 585/640; 422/147
(58) Field of Classification Search ........... 585/640; 422/147
    See application file for complete search history.

(56) References Cited

U.S. PATENT DOCUMENTS

| | | | |
|---|---|---|---|
| 4,440,871 A | 4/1984 | Lok et al. | 502/214 |
| 4,873,390 A | 10/1989 | Lewis et al. | 585/638 |
| 5,095,163 A | 3/1992 | Barger | 585/640 |
| 5,126,308 A | 6/1992 | Barger et al. | 502/214 |
| 5,191,141 A | 3/1993 | Barger et al. | 585/640 |
| 5,744,680 A | 4/1998 | Mulvaney, III et al. | 585/640 |
| 6,166,282 A | 12/2000 | Miller | 585/638 |
| 6,403,854 B1 | 6/2002 | Miller et al. | 585/638 |

FOREIGN PATENT DOCUMENTS

GB    1 538 874    *    1/1979

OTHER PUBLICATIONS

Chemical Engineers' Handbook, 5th Edition, pp. 20-69 to 20-70, McGraw-Hlll Book Company, 1973.*

* cited by examiner

*Primary Examiner*—In Suk Bullock
(74) *Attorney, Agent, or Firm*—Mark Goldberg

(57) ABSTRACT

The present invention comprises a process and apparatus for producing olefins from oxygenates in a reactor. This process comprises these oxygenates with a catalyst to produce a gaseous mixture comprising light olefins and by-products, sending the mixture to a single stage cyclone within said reactor to separate said catalyst from said gaseous mixture and then sending said the to a second stage cyclone. The second stage cyclone is located outside of said reactor and it functions to remove the catalyst from the mixture. Then the catalyst can be returned to the reactor after having been treated in a regeneration zone to remove carbonaceous deposits from the catalyst.

4 Claims, 2 Drawing Sheets

EXTERNAL SECOND STAGE CYCLONES IN OLEFIN PRODUCTION PROCESS

CROSS-REFERENCE TO RELATED APPLICATION

This application claims priority from Provisional Application Ser. No. 60/624,032 filed Nov. 1, 2004, the contents of which are hereby incorporated by reference.

FIELD OF INVENTION

The present invention relates generally to an Oxygenate-To-Olefin (OTO) Process utilizing a fluidized oxygenate conversion zone and a relatively expensive catalyst containing an ELAPO molecular sieve. More particularly, the invention relates to a method of removing catalyst particles from a particle effluent vapor stream.

BACKGROUND OF INVENTION

A major portion of the worldwide petrochemical industry is concerned with the production of light olefin materials and their subsequent use in the production of numerous important chemical products via polymerization, oligomerization, alkylation and the like well-known chemical reactions. Light olefins include ethylene, propylene and mixtures thereof. These light olefins are essential building blocks for the modern petrochemical and chemical industries. The major source for these materials in present day refining is the steam cracking of petroleum feeds. The art has long sought a source other than petroleum for the massive quantities of raw materials that are needed to supply the demand for these light olefin materials. A great deal of the prior art's attention has been focused on the possibility of using hydrocarbon oxygenates and more specifically methanol as a prime source of the necessary alternative feedstock. Oxygenates are particularly attractive because they can be produced from such widely available materials as coal, natural gas, recycled plastics, various carbon waste streams from industry and various products and by-products from the agricultural industry. The art of making methanol and other oxygenates from these types of raw materials is well established and typically involves the use of one or more of the following procedures: (1) manufacture of synthesis gas by any of the known techniques typically using a nickel or cobalt catalyst followed by the well-known methanol synthesis step using relatively high pressure with a copper-based catalyst; (2) selective fermentation of various organic agricultural products and by-products in order to produce oxygenates; or (3) various combinations of these techniques.

The art has focused on different procedures for catalytically converting oxygenates such as methanol into the desired light olefin products. These light olefin products must be available in quantities and purities such that they are interchangeable in downstream processing with the materials that are presently produced using petroleum sources. The art has developed a methanol-to-olefins (MTO) conversion technology based on the use of a non-zeolitic molecular sieve catalytic material. This MTO art is perhaps best illustrated by reference to UOP's extensive work in this area as reported in numerous patents of which U.S. Pat. Nos. 5,095,163; 5,126,308 and 5,191,141 are representative. This approach to MTO conversion technology was primarily based on using a catalyst system comprising a non-zeolitic molecular sieve, generally a metal aluminophosphate (ELAPO) and more specifically a silicoaluminophosphate molecular sieve (SAPO), with a strong preference for a SAPO species that is known as SAPO-34. This SAPO-34 material was found to have a very high selectivity for light olefins with a methanol feedstock and consequently very low selectivity for the undesired corresponding light paraffins and the heavier materials. This ELAPO catalyzed MTO approach is known to have at least the following advantages relative to the zeolitic catalyst route to light olefins: (1) greater yields of light olefins at equal quantities of methanol converted; (2) capability of direct recovery of polymer grade ethylene and propylene without the necessity of the use of extraordinary physical separation steps to separate ethylene and propylene from their corresponding paraffin analogs; (3) sharply limited production of by-products such as stabilized gasoline; (4) flexibility to adjust the product ethylene-to-propylene weight ratios over the range of 1.5:1 to 0.75:1 by minimal adjustment of the MTO conversion conditions; and (5) significantly less coke make in the MTO conversion zone relative to that experienced with the zeolitic catalyst system.

For various reasons well articulated in UOP's patents, U.S. Pat. Nos. 6,403,854; 6,166,282 and 5,744,680 (all of the teaching of which are hereby specifically incorporated by reference) the consensus of the practitioners in this OTO or MTO art points to the use of a fluidized reaction zone along with a fluidized regeneration zone as the preferred commercial solution to the problem of effectively and efficiently using an ELAPO or SAPO-type of catalyst system. As is well-understood by those of skill in the fluidization art, the use of this technology gives rise to a substantial problem of solid-vapor separation in order to efficiently separate the particles of the fluidized catalyst from the vapor products of the OTO or MTO reaction as well as from any unreacted oxygenate materials exiting the OTO or MTO conversion zone. Standard industry practice for accomplishing this difficult separation step involves its use of one or more vapor-solid cyclonic separating means which are well illustrated in the sole drawing of U.S. Pat. No. 6,166,282 where a series of three cyclonic separation means are used to separate spent OTO or MTO catalyst from the product effluent stream.

Despite the promising developments associated with the ELAPO or SAPO catalyzed routes to light olefins there, are still substantial hurdles to overcome before an economically attractive OTO or MTO process can be fully realized. Coking of surfaces within the reactor can reduce yield and productivity of these processes. Two particular potential coking problems are discussed herein. One coking problem to resolve is the coking of surfaces as the result of reactive materials remaining in stagnant zones within the reactor. A second coking problem can be the result of recycling of unreacted oxygenate together with recycling of various reaction by-products combined with the oxygenate feed stream. Both of these problems have now been resolved. A significant problem has been resolved by the present invention. In previous designs, there have been consecutive stages of cyclones for separation of catalyst particles from product effluent gas. Such a design is susceptible to difficulties caused by pressure drop with the two stages of cyclones. In addition, in the event of an unexpected surge in pressure, such a design is susceptible to a significant loss of catalyst. The present invention also addresses this problem.

SUMMARY OF THE INVENTION

The present invention comprises a process and apparatus for producing olefins from oxygenates in a reactor. This process comprises these oxygenates with a catalyst to produce a gaseous mixture comprising light olefins and by-products, sending the mixture to a single stage cyclone within said reactor to separate said catalyst from said gaseous mixture and then sending said the to a second stage cyclone. The second stage cyclone is located outside of said reactor and it functions to remove the catalyst from the mixture. Then the catalyst can be returned to the reactor after having been treated in a regeneration zone to remove carbonaceous deposits from the catalyst.

Other objects, embodiments, advantages and features of the present invention will be clear to someone of ordinary skill in the chemical engineering art from a detailed examination of the following description of the invention as well as the attached drawings.

TERMS AND CONDITIONS DEFINITIONS

Figure 1:
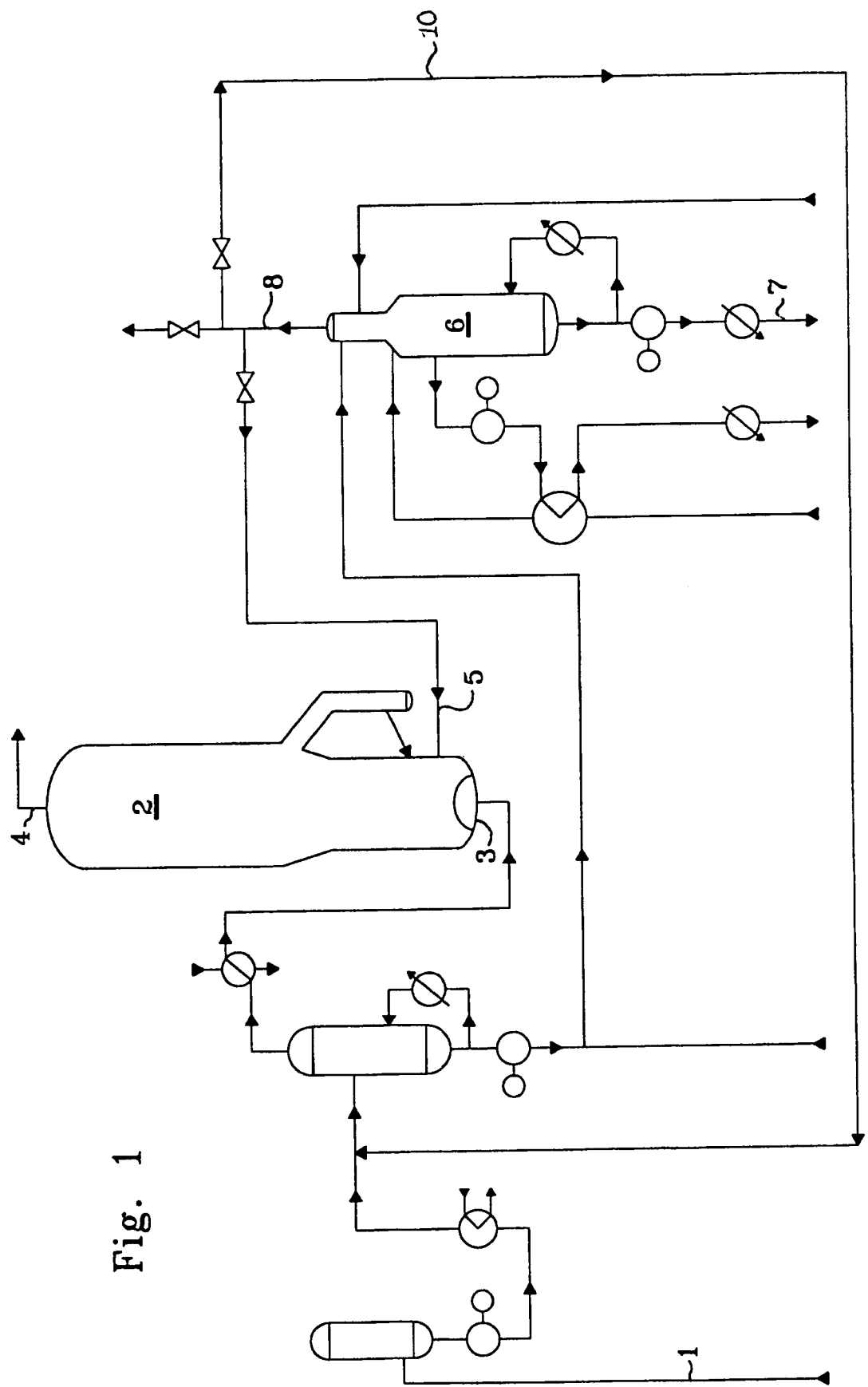
FIG. 1 is a process flow diagram showing the reactor with separate injection of recycled oxygenate from the main feed stream.

The following terms and conditions are used in the present specification with the following meanings: (1) a "portion" of a stream means either an aliquot part that has the same composition as the whole stream or a part that is obtained by eliminating a readily separable component therefrom (e.g. if the stream contains hydrocarbons in admixture with steam, then after condensation of a major portion of the steam, it comprises an aqueous portion and a hydrocarbon portion). (2) an "overhead" stream means the net overhead recovered from the specified zone after recycle of any portion to the zone for reflux or any other reason. (3) a "bottom" stream means the net bottom stream from the specified zone obtained after recycle of any portion for purposes of reheating and/or reboiling and/or after any phase separation. (4) a line is "blocked-off" when it contains a valve that is set to a position that prevents flow through the line. (5) presence of necessary compressors and/or pumps is understood when flow is shown from a zone of relatively low pressure to a zone of higher pressure. (6) presence of necessary heating and/or cooling means is implied when flow is shown between zones operating at different temperatures. (7) an ingredient is "lifted" or "stripped" when it is concentrated in the overhead stream withdrawn from the specified zone. (8) a "vapor" stream means a stream containing one or more components in the gaseous state. (9) the term "light olefins" means ethylene, propylene and mixtures thereof. (10) The expression "ELAPO" molecular sieve means a material having a three-dimensional microporous framework structure of $ALO_2$, $PO_2$ and $ELO_2$ tetrahedral units having the empirical formula:

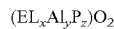

where EL is a metal selected from the group consisting of silicon, magnesium, zinc, iron, cobalt, nickel, manganese, chromium and mixtures thereof, x is the mole fraction of EL and is at least 0.005, y is the mole fraction of Al and is at least 0.01 z is the mole fraction of P and is at least 0.01 and x+y+z=1. When EL is a mixture of metals, x represents the total amount of the metal mixture present. Preferred metals (EL) are silicon, magnesium and cobalt with silicon being especially preferred. (11) The expression "SAPO molecular sieve" means an ELAPO molecular sieve wherein the EL element is silicon as described in U.S. Pat. No. 4,440,871. (12) The expression "OTO" process means a process for converting an oxygenate to light olefins and in a preferred embodiment when the oxygenate is methanol the OTO process is referred to as an MTO process herein. (13) The term "oxygenate" means an oxygen-substituted aliphatic hydrocarbon preferably containing 1 to 10 carbon atoms. (14) A reagent is "compatible" with a catalyst system when the physical, chemical and catalytic properties of the catalyst are not permanently altered by interaction with the reagent.

DETAILED DESCRIPTION OF THE INVENTION

In the instant OTO process, the feed stream comprises one or more oxygenates. The term "oxygenate" is employed herein to include alcohols, ethers, and carbonyl compounds (e.g. aldehydes, ketones, carboxylic acids, and the like). The oxygenate feedstock preferably contains at least one oxygen atom and about 1 to 10 carbon atoms and, and preferably, contains from about 1 to 4 carbon atoms. Suitable oxygenates include lower straight or branched chain alkanols, and their unsaturated counterparts. Representatives of suitable oxygenate compounds include methanol, dimethyl ether (DME), ethanol, diethyl ether, methylether, formaldehyde, dimethyl ketone, acetic acid, and mixtures thereof.

In the OTO conversion step of the present invention, the oxygenate feedstock is catalytically converted to hydrocarbons containing aliphatic moieties such as—but not limited to—methane, ethane, ethylene, propane, propylene, butylene, and limited amounts of other higher aliphatics including di-olefins by contacting the feedstock with a an ELAPO-containing catalyst. A diluent is not required but is a useful option to maintain the selectivity of the catalyst to produce light olefins, particularly ethylene and propylene. The use of a diluent such as steam can provide certain equipment cost and thermal efficiency advantages as well as lowering the partial pressure of the oxygenate reactants, thereby increasing selectivity to olefins. The phase change between steam and liquid water can also be employed to advantage in transferring heat between the feedstock and the reactor effluent, and the separation of the steam diluent from the product requires simple condensation of the water to separate the water from the hydrocarbons. Ratios of 1 mole of oxygenates to about 0.1 to 5 moles of diluent have been disclosed as being useful in the OTO conversion reaction. The preferred diluent is steam.

The oxygenate conversion step of the present invention is preferably conducted such that the oxygenate feedstock is contacted in a vapor phase in a reaction zone with a ELAPO molecular sieve catalyst at effective conversion conditions to produce olefinic hydrocarbons, i.e., an effective temperature, pressure, weight hourly space velocity (WHSV) and, optionally, an effective amount of diluent. The OTO step is affected for a period of time sufficient to produce the desired light olefin products. The oxygenate conversion step is effectively carried out over a wide range of pressures, including autogenous pressures. The temperature which may be employed in the oxygenate conversion step may vary over a wide range depending, at least in part, on the selected ELAPO molecular sieve catalyst. In general, the OTO step can be conducted at an effective temperature between about 350° and about 600° C.

In the oxygenate conversion step of the present invention, it is preferred that the ELAPO catalysts have relatively small pores. Preferably, the small pore catalysts have a substantially uniform pore structure, e.g., substantially uniformly sized and shaped pore with an effective diameter of less than about 5 angstroms. Suitable catalyst may comprise an ELAPO molecular sieve and a matrix material. A preferred ELAPO molecular sieve is one in which the element (EL) content varies from about 0.005 to about 0.2 mole fraction and in which EL is silicon (usually referred to as SAPO). The SAPOs which can be used in the instant invention are preferably any of those described in U.S. Pat. Nos. 4,440,871; 5,126,308 and 5,191,141 (all of which are hereby specifically incorporated by reference). Especially preferred SAPOs include the SAPO-34 and SAPO-17 structures with SAPO-34 being most preferred.

The ELAPO catalyst is preferably incorporated into solid particles containing one or more matrix materials in which the catalyst is present in an amount effective to promote the desired oxygenate conversion reactions. In one aspect, the solid particles comprise a catalytically effective amount of the catalyst and at least one matrix material, preferably selected from the group consisting of binder materials, filler materials, and mixtures thereof in an amount selected to provide desired properties, e.g., desired catalyst dilution, mechanical strength, and the like to the solid particles. Such matrix materials are preferably porous in nature and may contribute to or promote one or more of the desired oxygenate conversion reactions—particularly the conversion of methanol to DME. The preparation of solid particles comprising ELAPO catalyst and matrix materials in a fluidized size range is conventional and well known in the spray drying art and, therefore, need not be discussed in detail herein.

During the oxygenate conversion reactions, a carbonaceous material, i.e., coke, is deposited on the catalyst in an amount of about 1 to 20 mass-% and more commonly about 1.5 to 9 mass-%. The carbonaceous deposit material has the effect of reducing the number of available active sites on the catalyst which thereby affects the extent of the conversion. During the OTO conversion step a portion of the coked catalyst is withdrawn from the OTO reaction zone and passed to a regeneration step where it is regenerated with an oxygen-containing medium (e.g. air) to remove at least a portion of the carbonaceous material and returned to the oxygenate conversion reaction zone. Regeneration conditions can be varied moreover depending upon the type of ELAPO catalyst used and the type of contaminant material present upon the catalyst prior to its regeneration. See U.S. Pat. No. 4,873,390 for additional information on oxidation regeneration techniques for ELAPO catalysts.

The problem of recovery of ELAPO catalyst particles from the product effluent stream withdrawn from the OTO conversion zone is a problem that is unique to a fluidized bed type of system. In a fluidized system, large amounts of finely divided catalyst particles are continuously transported between a reaction zone and a regeneration zone and in the OTO reaction zone they are admixed with the oxygenate feed stream in an amount which is conveniently measured in terms of a WHSV calculated on the basis of mass hourly flow rate of the sum of the mass of oxygenate reactants passed to the MTO conversion zone plus any other oxygenate or hydrocarbon reactants present in the feed or recycle streams divided by the mass of the ELAPO catalyst present in the OTO conversion zone. WHSV for use in the fluidized in the OTO conversion zone associated with the present invention can range from about 0.1 to about 100 $hr^{-1}$ with best results obtained within the range of about 0.5 to 40 $hr^{-1}$. Since the OTO conversion reactions are strongly exothermic, a significant temperature increase will occur across the OTO reaction zone which is ordinarily of the magnitude of about 100° to 400° C. (180° to 720° F.) and thus unlike traditional hydrocarbon FCC practice, the catalyst circulation rate is not set on the basis of the amount required to provide sufficient heat to the endothermic reactions that are traditionally involved in hydrocarbon FCC practice. In a fluidized OTO reactor system, the catalyst circulation rate between the reactor and the regenerator will ordinarily be set at a minimum level designed to hold average coke on the circulating catalyst inventory of the ELAPO catalyst entering the conversion step in the range of about 1 to 20 mass-% of the active ingredient in the catalyst and more preferably in the range of about 1.5 to 9 mass-%. The fluidized catalyst being recirculated to the OTO conversion reactor must be intimately admixed with the vaporous oxygenate containing feed stream for a period of time dictated by the desired WHSV and thereafter the resulting vapor-solid mixture must be quickly separated in order to provide a stream of deactivated catalyst that at least in part can be charged to the regeneration zone, thereby completing the catalyst circulation loop. In order to achieve proper fluidization of the ELAPO catalyst system used in the OTO conversion zone, it is necessary to provide the catalyst particles in a particle size distribution in the range of about 1 to 150 microns with the average particle size usually set in the range of about 20 to 100 microns and preferably in the range of about 65 to 85 microns. Due to the opportunities that the catalyst particles have for interacting with each other and the walls of the OTO reactor, its associated regenerator and transport lines the particle size distribution over time will degrade with the generation of a significant amount of catalyst fines due to the abrasive environment experienced in the internal or external catalyst circulation loops. Best practice with respect to OTO reactor configuration is a fluidized bed catalyst system with a fast-fluidized reactor system being particularly preferred. A good example of a prior art fast-fluidized OTO reactor system is shown in U.S. Pat. No. 6,166,282 (the teachings of this '282 patent are specifically incorporated herein by reference). These teachings provide additional details such as the preferred superficial vapor velocity for proper operation of the OTO conversion zone. It is particularly to be noted that the '282 patent incorporates within reactor vessel 10 shown in its drawing three stages of vapor-solid catalyst separation. In the instant invention, it has now been found that at least one of these stages can be located in a separate surge vessel. The first stage is shown at the top of riser zone 26 wherein the mixture of ELAPO catalyst particles and OTO reaction product stream is discharged through distributor arms 24 into a separation vessel 22 which provides a cyclonic separation action due to the tangential discharge of this mixture of reaction products and catalyst particles. The second stage of vapor-solid separation illustrated in the drawing of this '282 patent is the first cyclone 20 wherein a mixture of fluidized catalyst particles and reaction products is shown as being separated into an overflow vapor stream and a down flowing catalyst particle stream. The third stage of the separation is shown in the drawing of the '282 patent by the operation of closed-couple cyclone separating means 21 which receives as input the overflow stream from the cyclone separating means 20 and produces a second overflow stream which is shown as vented into the overhead plenum of the OTO reaction zone exiting the OTO reaction zone as effluent stream 48. Despite this three-stage separation operation provided by the preferred fast-fluidized reactor zone illustrated in the '282 patent, the resulting vaporous product effluent stream withdrawn from OTO reactor zone 10 via line 48 still contains significant quantities of the OTO conversion catalyst. Depending on the exact fluidization conditions that are utilized in an OTO reaction zone of the type shown in the '282 patent, the product effluent stream withdrawn therefrom can contain catalyst particles in an amount corresponding to 0.01 to 0.1 mass-% with a more typical value being about 0.015 to about 0.05 mass-% of this product effluent stream. Although these quantities of effluent-contaminating catalyst particles appear to be quite small, they represent over time a significant loss of the relatively expensive ELAPO catalyst system (relatively expensive is meant to be relative to the zeolitic catalyst systems such as the ZSM-5 catalyst of the prior art). The presence of these contaminating catalyst particles in the product effluent stream give rise to a substantial need for a method for separating and recovery of the catalytic value of these effluent contaminating catalyst particles.

In the present invention, it has been found advantageous to have a single stage of cyclones within the reactor vessel and separate single stage cyclones downstream of the reactor to capture catalyst during upsets. A separate vessel, referred to herein as a reactor surge vessel is provided downstream of the reactor. A product effluent stream that contains catalyst particles is sent outside of the reactor vessel to the reactor surge vessel. Within the reactor surge vessel are single stage cyclones for separation of the catalyst particles from the effluent. The reactor effluent is sent out the top of the cyclones and then out the top of the reactor surge vessel for further processing. The catalyst that has been removed by use of these cyclones can now be recycled to the main reactor. If desired, the catalyst can be held in a catalyst hopper for return to the reactor as necessary. In addition to the removal of the catalyst by the cyclones, some of the catalyst particles will drop out of the effluent gas within the reactor surge vessel before entering the cyclones. Among the advantages of having the second stage of cyclones separated from the first stage cyclones in the reactor, the diplegs of the second stage cyclones have less pressure drop to overcome than if they would be in immediate series within the same reactor vessel. In addition, having the second stage of cyclones outside of the reactor allows for the product throughput to be increased within the reactor since throughput is limited by vessel size and the process is operated at maximum capacity. The two-stage system of this invention is estimated to reduce catalyst loss to about 100 lbs/hr in a comparable one-stage system.

DETAILED DESCRIPTION OF THE DRAWINGS

The following description of the present process is made with reference to the attached drawings. In the interest of simplifying the description of the invention in order to facilitate understanding, the drawings do not contain representations of heaters, heat exchangers, coolers, valves, control means and other conventional items that are well known to those of ordinary skill in the chemical engineering art except where their presence is essential to understanding the present invention.

The attached drawings illustrate the instant invention with components numbered as necessary to understand the invention. In FIG. 1 is shown a feed stream 1 that passes through several vessels and lines and is heated and sent to a distribution zone 3 of a reactor 2. Shown as relevant to the present invention, is a product gas stream 4 exiting the top of reactor 2 to be sent to a product separation zone (not shown). A recycle stream of oxygenates and by-products in line 5 is shown entering reactor 2 separate from feed stream 1. This recycle stream of oxygenates and by-products in line 5 is separated from a product stream 10 in an oxygenate stripper 6.

Oxygenate stripper 6 operates to strip any unreacted oxygenates such as methanol, DME and diolefins from the aqueous streams charged thereto and to produce a relatively pure water stream which is withdrawn from the bottom of the stripping zone via a line 7 and is available for further use in the process if for example it is desired to use an aqueous diluent in the operation of the reaction zone within reactor 2. Such diolefins, even in trace amounts, have been found to be the cause of significant degrees of undesired polymerization and fouling. Oxygenate stripper 6 is operated at oxygenate stripping conditions effective to produce an overhead vapor stream which exits oxygenate stripper 6 via a line 8 and comprises a significant portion of the net unreacted oxygenates recovered from the effluent stream and it can be recycled via line 5 which enters reactor 2 through nozzles or injection tubes that are about 3 to 6 cm in diameter in order to enhance the conversion of oxygenates without fouling of the feed distributor from diolefin polymerization and fouling.

Figure 2:
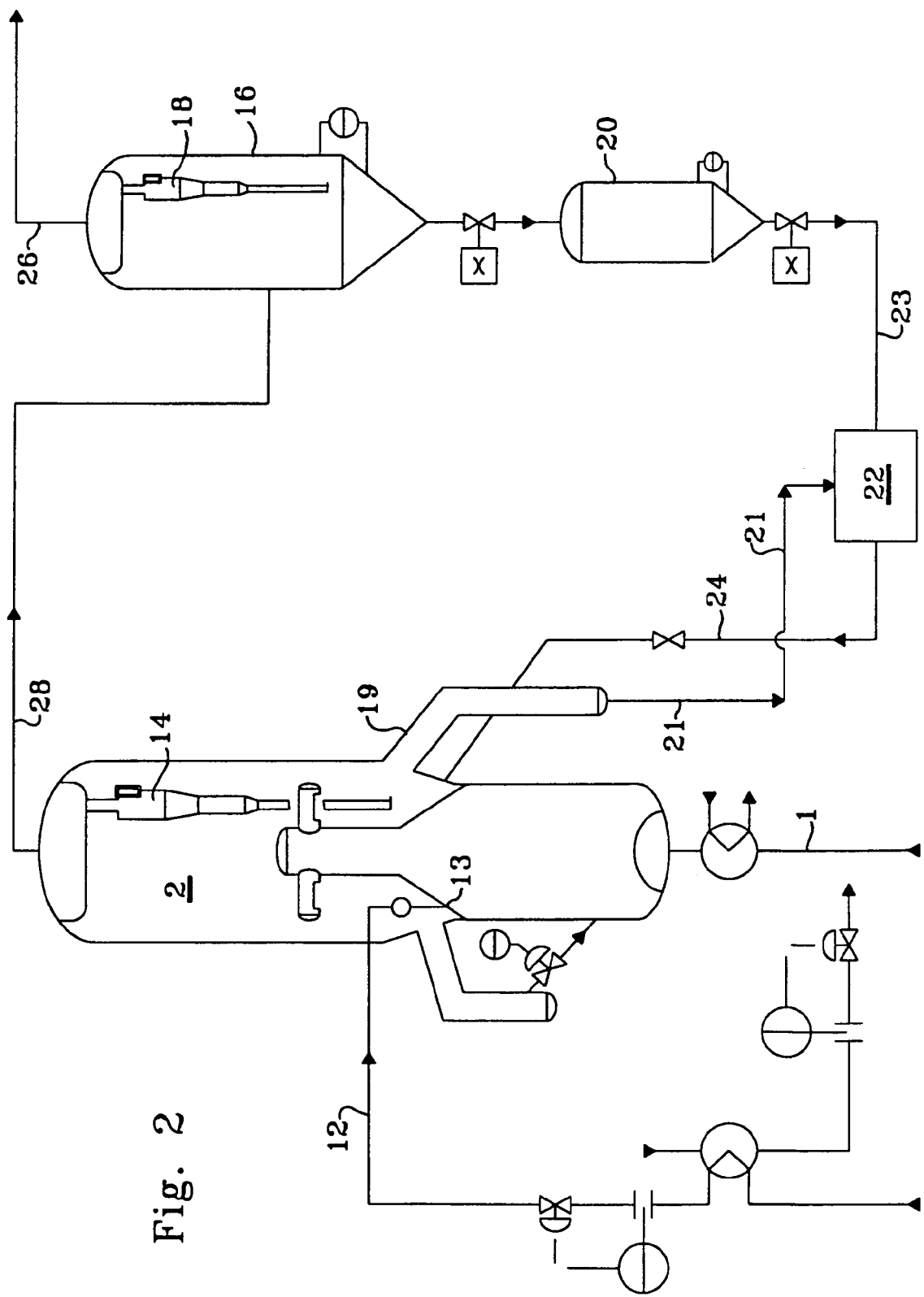
FIG. 2 is a process flow diagram showing the separate stage cyclones for removal of catalyst fines from product effluent and the purge of stagnant zones within the reactor.

In FIG. 2 is shown reactor 2 with feed stream 1 again entering the bottom of the reactor. A purge stream 12 is shown entering the reactor at a port 13. Within the reactor is a first stage cyclone 14 to separate catalyst from the product gas. The majority of the catalyst particles within the product gas are removed by this first stage cyclone with the catalyst passing down into the lower part of the reactor and the product gas going through a line 28 to a reaction surge vessel 16 having at least one cyclonic separation means 18 for further removal of the catalyst from the product stream. The catalyst falls from the cyclone and can be stored in a catalyst hopper 20. The catalyst is shown being sent through a regeneration zone 22 and returned to the reactor through a line 24. Optionally, the catalyst may be returned directly to the reactor. These cyclones are more broadly referred to as vapor-solid cyclonic separation. The product gas is seen exiting through a line 26.

A mixture of deactivated catalyst particles and olefinic reaction products is formed in the reactor. This mixture travels up the riser section of the reaction zone and goes through a series of vapor-solid separation operations to produce a stream of deactivated catalyst particles and a conversion zone product effluent stream containing light olefins, unreacted oxygenates, $H_2O$, other reaction products and undesired amounts of contaminating catalyst particles. During the course of the highly exothermic MTO reaction that occurs in the reaction zone of the reactor, a layer of carbonaceous material coats the outer surface of the catalyst particles and this layer of carbonaceous deposits acts to deactivate the catalyst particles at least in part to the extent that at least a portion of these catalyst particles must have their activity restored in associated catalyst regeneration zone 22. The spent catalyst passes through an outlet 19 to a line 21 and then to regeneration zone 22. These carbonaceous deposits are commonly referred to as "coke" and are customarily removed by an oxidation procedure. A catalyst stream then is returned to the reaction zone. At least a portion of the deactivated catalyst material recovered from the cyclonic separation means are stripped of volatile hydrocarbons and passed via a line 23 to regeneration zone 22 wherein at least a significant portion of the carbonaceous deposits are oxidatively removed with resulting production of a stream of regenerated catalyst particles which flow via line 24 back to the reaction zone for further use in converting feed stream 1. A relatively small proportion (usually less than 1%) of the catalyst returned to the regeneration zone passes through line 24. Despite the use of one or more vapor-solid cyclonic separation means in the reaction zone to scrub the catalyst particles from the product effluent stream, there is in actual practice still a significant amount of catalyst particles that are present in the product effluent stream. It has been found effective to locate further cyclonic separation means 18 for further removal of the catalyst particles from the product effluent stream. These contaminating catalyst particles can be recovered by a quench tower located upstream of the downstream compression means. The degree of contamination of the product effluent stream by these catalyst particles corresponds to about 0.01 to 0.1 mass-% of the effluent product stream and therefore represents a substantial source of continuing catalyst loss from the catalyst inventory that circulates in and through the MTO conversion zone in reactor 2 and the associated catalyst regeneration zone.

For purposes of the present invention, we prefer to use liquid-solid cyclones or hydrocyclones for this application in view of their efficiency and relatively low capital and operating costs but any other suitable liquid-solid separating means can be used for their applications if locally available.

What is claimed is:

1. A process for producing olefins from oxygenates in a reactor, said process comprising:
    a) contacting said oxygenates with a catalyst to produce a gaseous mixture comprising light olefins and by-products;
    b) sending said mixture to a single stage cyclone system within said reactor to separate said catalyst from said gaseous mixture;
    c) sending said gas to a second stage cyclone system wherein said second stage cyclone system is enclosed within a reactor surge vessel and is located outside of said reactor and wherein said second stage cyclone system functions to remove said catalyst from said gaseous mixture; and
    d) returning said recovered catalyst to said reactor.

2. The process of claim 1 wherein catalyst is sent from said second stage cyclone system to said reactor.

3. The process of claim 2 wherein said catalyst is first sent to a catalyst hopper prior to being sent to said reactor.

4. The process of claim 1 wherein said catalyst is sent to a regeneration zone and then returned to said reactor.

\* \* \* \* \*